US00PP32490P3

(12) United States Plant Patent
Beckman

(10) Patent No.: US PP32,490 P3
(45) Date of Patent: Nov. 17, 2020

(54) CALLA LILY PLANT NAMED 'DIVA HIMALAYA'

(50) Latin Name: *Zantedeschia aethiopica*
Varietal Denomination: Diva Himalaya

(71) Applicant: Dümmen Group B.V., De Lier (NL)

(72) Inventor: Peter Beckman, Santa Cruz, CA (US)

(73) Assignee: Dümmen Group B.V., De Lier (NL)

( * ) Notice: Subject to any disclaimer, the term of this patent is extended or adjusted under 35 U.S.C. 154(b) by 0 days.

(21) Appl. No.: 16/602,427

(22) Filed: Oct. 2, 2019

(65) Prior Publication Data

US 2020/0113108 P1 Apr. 9, 2020

Related U.S. Application Data

(60) Provisional application No. 62/766,213, filed on Oct. 5, 2018.

(51) Int. Cl.
*A01H 5/02* (2018.01)
*A01H 6/56* (2018.01)

(52) U.S. Cl.
USPC ..... Plt./490
CPC ..... *A01H 6/56* (2018.05)

(58) Field of Classification Search
USPC ..... Plt./490
CPC ..... A01H 5/02
See application file for complete search history.

*Primary Examiner* — Annette H Para
(74) *Attorney, Agent, or Firm* — The Webb Law Firm

(57) ABSTRACT

'Diva Himalaya' is a new variety of calla lily plant having white colored spathes and thin, strong peduncles. The leaves are green with no maculations present.

1 Drawing Sheet

Botanical classification: *Zantedeschia aethiopica.*
Varietal denomination: 'Diva Himalaya'.

BACKGROUND OF THE NEW PLANT

The present invention comprises a new and distinct cultivar of calla lily, botanically known as *Zantedeschia aethiopica* and hereinafter referred to by the cultivar name 'Diva Himalaya'.

'Diva Himalaya' is a product of a planned breeding program and the new cultivar was selected in Santa Cruz, Calif. from the F2 population of the crossing of unpatented *Zantedeschia* seedling 7043-BK (female parent) with unpatented *Zantedeschia* seedling 94109-56 (male parent). When compared to its female parent, the blooms of 'Diva Himalaya' are more white in color, smaller, and exhibit earlier maturity. Further, the slim, strong flower stems of 'Diva Himalaya' are easier to pull at harvest. The leaves of 'Diva Himalaya' are smaller and more dense than its female parent. When compared to its male parent, the blooms of 'Diva Himalaya' are larger, with a better wrapped and formed spathe. Further, the overall plant size and leaves of 'Diva Himalaya' are larger than its male parent.

The new variety was initially asexually reproduced through tissue culture propagation in Santa Cruz, Calif. Asexual reproductions of 'Diva Himalaya' have demonstrated that the combination of characteristics as herein disclosed for the new variety are retained and reproduced true to type through successive generations of asexual reproduction.

Color references are made to The 2001 R.H.S. Colour Chart of The Royal Horticultural Society of London, 4$^{th}$ Edition, except where general color terms of ordinary significance are used.

The present invention has not been evaluated under all possible environmental conditions. The phenotype may vary with variations in environment without a change in the genotype of the plant.

The following traits have been repeatedly observed and determined to be basic characteristics of 'Diva Himalaya' which, in combination, distinguish this calla lily as a new and distinct cultivar:

1. White colored spathes;
2. No leaf maculations;
3. Early production time;
4. Thin, strong peduncles; and
5. Easy to transport.

Table 1 provides a comparison of 'Diva Himalaya' to similar *Zantedeschia aethiopica* varieties 'Avalanche' (unpatented) and 'Innocence' (unpatented).

TABLE 1

| Comparison variety | Differing trait(s) | Comparison expression | Present variety expression |
|---|---|---|---|
| 'Avalanche' | Leaf maculations | Present | None present |
| 'Innocence' | Spathe color | White Group RHS 155B | White Group RHS 155D |

BRIEF DESCRIPTION OF THE DRAWING

The accompanying photographic drawing illustrates the new variety, with the colors being as nearly true as is possible with color illustrations of this type.

DESCRIPTION OF THE NEW PLANT

Type: Evergreen.

*Form.*—Upright and semi-spreading.

*Height of leaf canopy above the soil.*—40-60 cm.

*Height of top of inflorescences above the soil*.—50-75 cm.

*Number of inflorescences per tuber*.—14-16 cm in diameter: 3-4. 18-20 cm in diameter: 4-5. 20-22 cm in diameter: 5-9.

*Lastingness of inflorescences on the plant*.—14-24 days.

*Main use*.—Potted plant and cut flower.

*Production time*.—Early, after 18-24 weeks.

*Disease/pest resistance*.—Very strong tolerance to Pythium root rot and bacteria soft rot.

*Transport*.—Easy.

*Root color*.—White.

*Berries*.—None present.

Leaves:

*Width*.—10-15 cm.

*Length*.—15-25 cm.

*Shape*.—Ovate.

*Apex*.—Apiculate.

*Base*.—Rounded.

*Margin*.—Entire.

*Color*.—Upper surface: Green Group RHS 137B, with no maculations present. Lower surface: Green Group RHS 137C, with no maculations present.

*Surface texture*.—Smooth (both surfaces).

*Leaf venation*.—None/indistinct.

*Petiole*.—Length: 25-45 cm. Diameter: 0.4-0.8 cm. Texture: Smooth. Shape: Very slim columnar. Color: The base is Green Group RHS 137B and the upper portion is Green Group RHS 137C.

Spathe:

*Length*.—9-12 cm.

*Width*.—6.5-8 cm.

*Height*.—10-14 cm.

*Fragrance*.—Slightly sweet.

*Shape*.—Funnel, with a slightly open back.

*Texture*.—Smooth.

*Apex*.—Pointed.

*Base*.—Continuous.

*Margin*.—Entire.

*Throat spot*.—Absent.

*Color*.—White Group RHS 155D (upper and lower surfaces).

Spadix:

*Length*.—5-7 cm.

*Diameter*.—0.4-0.6 cm.

*Color*.—Yellow Group RHS 13A to 13B.

*Position relative to spathe*.—Upright from base.

*Apex*.—Apiculate.

*Location of female organs*.—Upper portion of spadix.

*Location of male organs*.—Lower portion of spadix.

*Pistil number*.—Numerous, more than 20.

*Pollen color*.—White Group RHS 155A to 155B.

Peduncles:

*Diameter*.—Thin.

*Strength*.—Strong.

*Color*.—Green Group RHS 137A to Yellow-Green Group RHS 144A.

I claim:

1. A new and distinct variety of calla lily plant named 'Diva Himalaya' as herein described and illustrated.

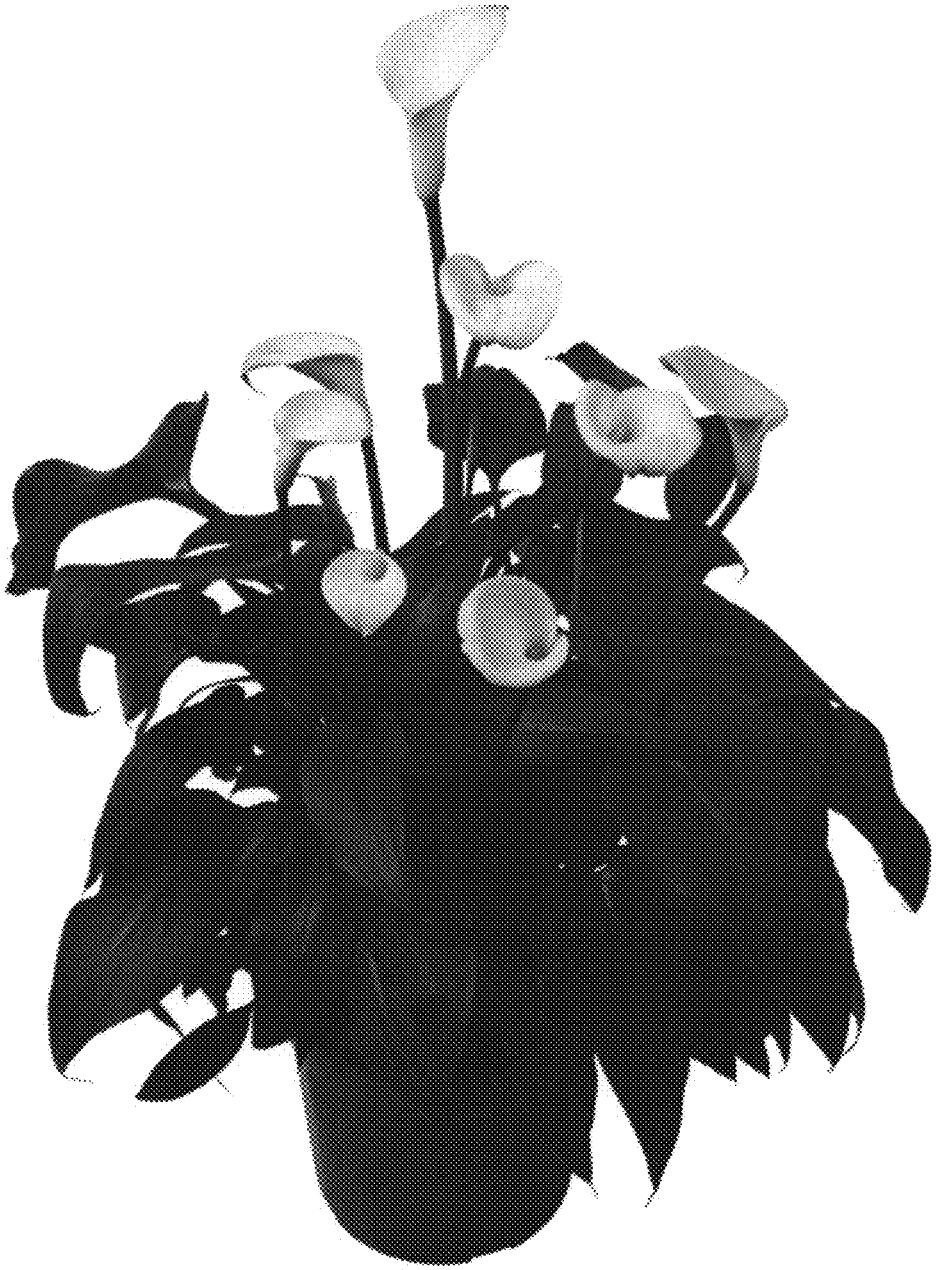

* * * * *